United States Patent
Dhaliwal

(10) Patent No.: US 11,000,397 B1
(45) Date of Patent: May 11, 2021

(54) SPINE ROLL TO PROMOTE MUSCULOSKELETAL ALIGNMENT AND STRENGTHENING OF A HUMAN SPINE

(71) Applicant: Amandeep Dhaliwal, Manteca, CA (US)

(72) Inventor: Amandeep Dhaliwal, Manteca, CA (US)

(*) Notice: Subject to any disclaimer, the term of this patent is extended or adjusted under 35 U.S.C. 154(b) by 459 days.

(21) Appl. No.: 16/147,423

(22) Filed: Sep. 28, 2018

Related U.S. Application Data

(60) Provisional application No. 62/764,016, filed on Jul. 16, 2018.

(51) Int. Cl.
*A61F 5/01* (2006.01)

(52) U.S. Cl.
CPC ..................... *A61F 5/01* (2013.01)

(58) Field of Classification Search
CPC .................. A61F 5/01; A61H 1/008
See application file for complete search history.

(56) References Cited

U.S. PATENT DOCUMENTS

| | | | |
|---|---|---|---|
| 4,686,968 A | 8/1987 | Scherger | |
| 5,987,675 A | 11/1999 | Kim | |
| 6,292,964 B1 | 9/2001 | Rose | |
| 6,357,066 B1 | 3/2002 | Pierce | |
| 6,969,114 B2 | 11/2005 | Keilhauer | |
| 2008/0248936 A1* | 10/2008 | Ferriss | A63B 26/003 482/142 |
| 2012/0065687 A1* | 3/2012 | Ballard | A61B 17/7011 606/259 |
| 2014/0090174 A1* | 4/2014 | Vladeta | A47C 7/40 5/633 |
| 2016/0136478 A1* | 5/2016 | Yu | A63B 21/0004 482/121 |
| 2017/0151117 A1* | 6/2017 | Chung | A61G 13/009 |
| 2019/0335905 A1* | 11/2019 | Alexander | A47C 7/46 |

* cited by examiner

*Primary Examiner* — Jan Christopher L Merene
*Assistant Examiner* — Cana A Gallegos
(74) *Attorney, Agent, or Firm* — Lumen Patent Firm

(57) ABSTRACT

A single structure device is provided to promote static and dynamic musculoskeletal alignment and strengthening of along the entire vertebral system. A vertebral surface pattern is defined for supporting the vertebral system extending as a continuous and varying surface pattern along its longitudinal axis. The vertebral surface pattern distinguishes a cranial-cervical region, a cervical, a thoracic region, a lumbar region, and a sacral region. The device is substantially circular allowing the device the ability to roll from side-to-side. The device could be solid, hollow, sectional or inflatable as long as the device is a single structure when in use to address and be used over the entire, and not just parts, of vertebral system.

20 Claims, 3 Drawing Sheets

SPINE ROLL TO PROMOTE MUSCULOSKELETAL ALIGNMENT AND STRENGTHENING OF A HUMAN SPINE

CROSS-REFERENCE TO RELATED APPLICATIONS

This application claims priority from U.S. Provisional Patent Application 62/764,016 filed Jul. 16, 2018, which is incorporated herein by reference.

FIELD OF THE INVENTION

This invention relates to devices to promote musculoskeletal alignment and strengthening of a vertebral system. In particular, this invention relates to devices to restore anatomically neutral postural and dynamic stability of the vertebral column and musculature.

BACKGROUND OF THE DESCRIPTION

Poor Posture has been linked to multiple health related problems like neck pain, back pain, forward head posture, headaches, poor overall health, fatigue, etc. Poor posture forces the spine to function in a poor alignment resulting in putting stress on all of its elements.

Foam devices are examples on how one could address posture related health problems. These devices could be cylindrical foam rollers or wedged-shaped structures in various shapes and sizes. A person would lay on top of these foam devices, supporting just a small portion of the spine, expecting the spine to realign itself. Unfortunately, these foam devices fail to properly align/contour with the natural shape and curves of the entire length of human spine/vertebral column. The limited support provided by these devices actually adds additional stress to the spine itself. Furthermore, these foam devices are typically used for static correction and would not be suitable or able to address any dynamic stability or posture issues.

The vertebral column functions most efficiently as a whole. Realignment of just one specific area of the spinal column can only lead to added stress on other areas and/or not address the problem completely. Therefore, the entire spine needs to be addressed as a whole for it to function optimally and provide the structure/support it is supposed to. The present invention provides a device to address the static and dynamic stability of the entire spine.

SUMMARY OF THE INVENTION

A device is provided to promote musculoskeletal alignment and strengthening of a vertebral system. The device is an elongated three-dimensional single structure defining a longitudinal axis between a first-end and a second-end. A vertebral surface pattern is defined for supporting the vertebral system extending as a continuous and varying surface pattern along the longitudinal axis in between the first and second ends. The elongated three-dimensional single structure is substantially circular and substantially symmetrical around the longitudinal axis and substantially retains its elongated three-dimensional structure when in use by a person. The circular structure allows the device the ability to roll around the longitudinal axis and the material retains the rolling ability when in use by a person.

In one example, the vertebral surface pattern distinguishes in a direction from the first-end to the second-end: a cranial-cervical region converging as the first-end point, a cervical region with a maximum cervical diameter, a thoracic region with a minimum thoracic diameter, a lumbar region with a maximum lumbar diameter, and a sacral region converging as the second-end point. The fact that the diameters of the cervical region and the lumbar region are larger than other parts of the device, allows the device the ability to roll specifically around both the cervical region and the lumbar region.

The regions are arranged such that their respective surfaces together define the continuous and varying vertebral surface pattern. In this structural design, the length defined along the longitudinal axis is shorter for the cervical region than for the lumbar region, and the length defined along the longitudinal axis is shorter for the cranial-cervical region than for the sacral region.

In one example, the maximum cervical diameter and the maximum lumbar diameter are substantially identical and both larger than the minimum thoracic diameter. In another example, the minimum thoracic diameter could be defined relative to either or both the maximum cervical diameter and the maximum lumbar diameter by a ratio of 0.3 to 0.6 or a ratio of 0.4 to 0.5.

In yet another example, the first-end diameter and the second-end diameter are substantially identical and smaller than the minimum thoracic diameter.

In yet another example, the surface could be textured or patterned.

In still another example, the device could be solid, hollow, sectional, inflatable, or a combination thereof as long as the device is a single structure when in use to provide promote musculoskeletal static and dynamic alignment and strengthening along the entire vertebral system.

Advantages of the spine roll can be defined as follows. The spine roll is designed to help re-align and restore natural/neutral curvature of the entire length of the human spine/vertebral column. The spine roll supports from the occipital area proximally to the distal end of the coccyx and it helps re-align every curvature in between these two regions. The spine roll can be made of material that has the ability to gently mold/shape itself with the extreme regions of the spine to add comfort while rigid enough to help support the curvature in a neutral position. The device could have a single uniform material, different multiple materials, one or more non-uniform materials, or combinations thereof.

The spine roll is designed with concave and convex curves that align accordingly with the curves of a neutral human spine/vertebral column. The spine roll has the ability to restore/realign each neutral curve from its extreme or diminished status. The spine roll has the ability to restore neutral alignment, which could help decrease stress/load on its elements caused by for example poor posture.

The spine roll has the ability to provide dynamic and static stability during a stretch or strengthening exercise. It is able to help relax the spinal muscles, stretch and strengthen the surrounding musculature during core stabilization or dynamic exercises through its ability to align parallel with the spine and roll perpendicular to the spine. The neutral spine roll helps emphasize the natural shape/alignment which is easier to sustain during and after exercise.

DETAILED DESCRIPTION

Example 1

Figure 1:
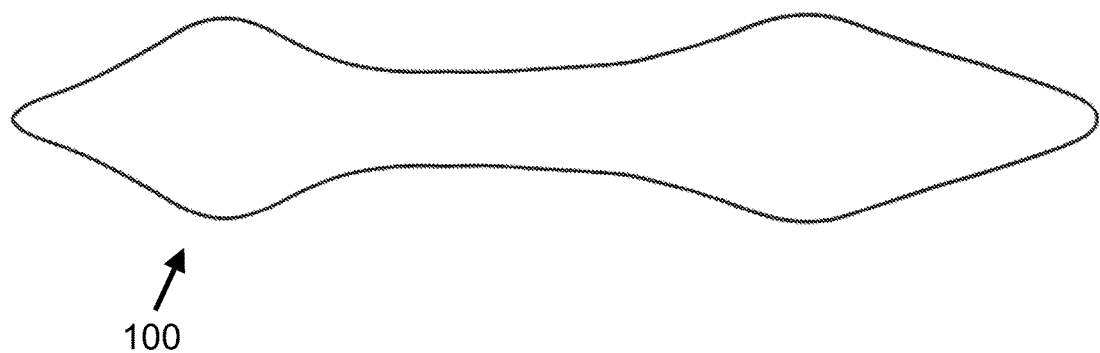
FIGS. 1-4 show according to exemplary embodiments of the invention a side (sagittal plane) view of the device specifying the vertebral surface pattern, the different regions making up the vertebral surface pattern, and examples of dimensions.
Figure 2:
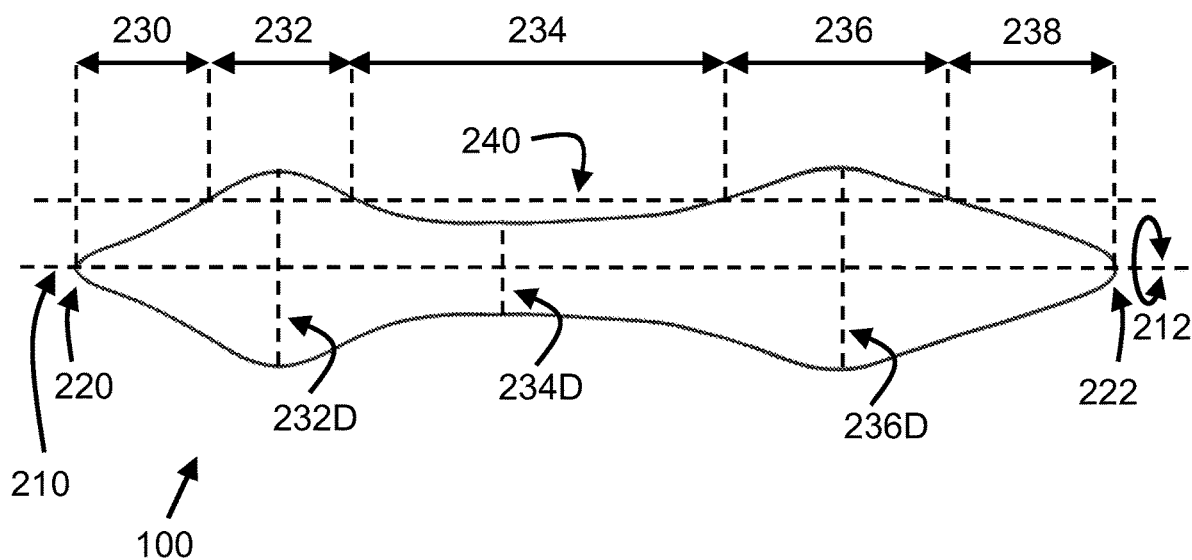

FIGS. 1-2 show a sagittal plane view of exemplary device 100 to promote musculoskeletal alignment and strengthening of a vertebral system. The sagittal plane view is defined in accordance when referring to human anatomy. Device 100 is an elongated three-dimensional structure defining a longitudinal axis 210 between a first-end 220 and a second-end 222. Device 100 is intended to mimic a vertebral surface pattern for supporting a vertebral system of a person (i.e. the back spine of a person from head-neck (cranial-cervical) to bottom (sacral)). The specific surface pattern could be derived from an average spinal curvature over multiple people such that the curvature, when a person lays on the device, aligns parallel to spine or vertebral structure.

Referring to FIG. 2, the support extends from a cranial-cervical region 230, cervical region 232, thoracic region 234, lumbar region 236 to a sacral region 238 (defined in reference to, for example, support-line 240). The support pattern is a continuous yet varying surface pattern along longitudinal axis 210 in between the first and second ends 220, 222. The elongated three-dimensional structure is substantially circular and substantially symmetrical around longitudinal axis 210 (i.e. transverse plane when referring to human anatomy) allowing the device the ability to roll around longitudinal axis 210 (i.e. side-to-side (see 212) for a person when laying on the device). Furthermore, when in use by a person the device substantially retains its elongated three-dimensional structure and therewith retains the rolling ability while in use. The circular pattern in the transverse plane might become a little more ellipsoidal, yet, and again, the device should be firm enough to retain its side-to-side rolling ability when in use.

More specifically, the vertebral surface pattern distinguishes different regions in a direction from first-end 220 to second-end 222 and defined by support-line 240:
  Cranial-cervical region 230 with an axis projected and defined along longitudinal axis 210 and converging as first-end 220 with a first-end diameter defined in a plane perpendicular to longitudinal axis 210,
  Cervical region 232 with a major axis projected and defined along longitudinal axis and with a maximum cervical diameter 232D defined in a plane perpendicular to longitudinal axis 210,
  Thoracic region 234 with a major axis projected and defined along longitudinal axis and with a minimum thoracic diameter 234D defined in a plane perpendicular to longitudinal axis 210,
  Lumbar region 236 with a major axis projected and defined along longitudinal axis and with a maximum lumbar diameter 236D defined in a plane perpendicular to longitudinal axis 210, and
  Sacral region 238 with an axis projected and defined along longitudinal axis 210 and converging as second-end point 220 with a second-end diameter defined in a plane perpendicular to longitudinal axis 210.

It is the arrangement of these regions in that particular order and with their respective surfaces that define the continuous and varying vertebral surface pattern.

Example 2

Figure 4:
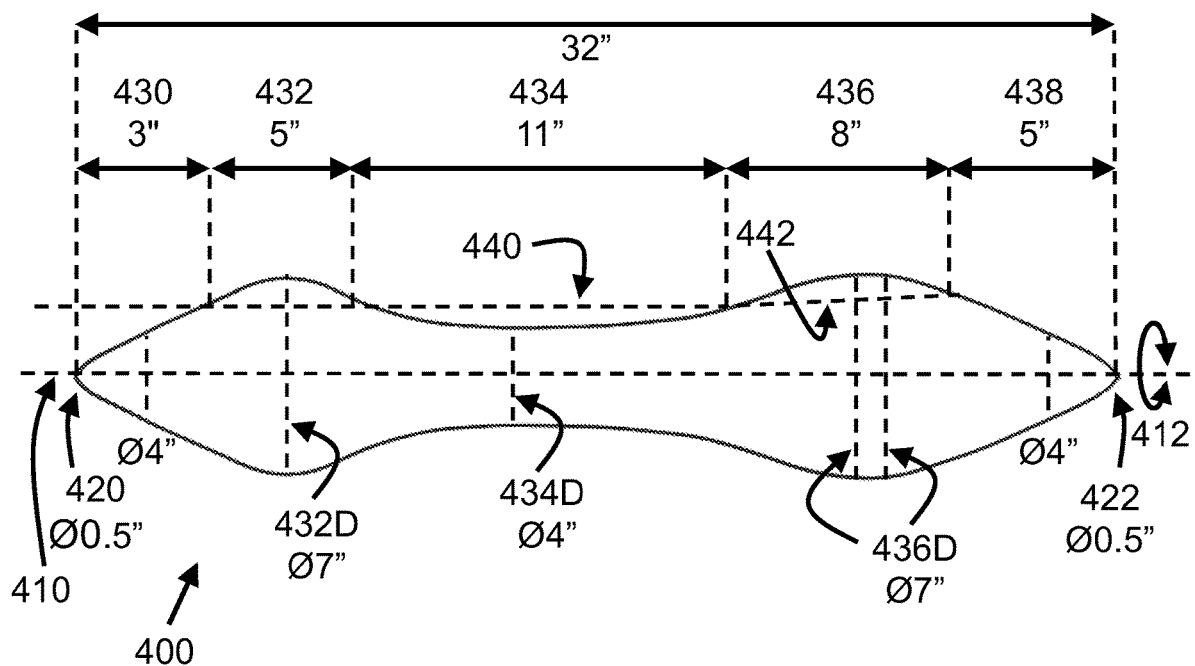

FIG. 4 shows a sagittal plane view of exemplary device 400 to promote musculoskeletal alignment and strengthening of a vertebral system. Device 400 differs from device 100 in dimension(s), specifically in some diameter sizes, a plateau (diameter) section for the lumbar region, and a more parabolic cranial-cervical and sacral regions. The sagittal plane view is defined in accordance when referring to human anatomy. Device 400 is an elongated three-dimensional structure defining a longitudinal axis 410 between a first-end 420 and a second-end 422. Device 400 is also intended to mimic a vertebral surface pattern for supporting a vertebral system of a person (i.e. the back spine of a person from head-neck (cranial-cervical) to bottom (sacral)). The specific surface pattern could be derived from an average spinal curvature over multiple people such that the curvature, when a person lays on the device, aligns parallel to spine or vertebral structure.

Referring to FIG. 4, the support extends from a cranial-cervical region 420, cervical region 422, thoracic region 434, lumbar region 436 to a sacral region 438 (defined in reference to, for example, support-lines 440 and 442). It is noted that support line 442 is sloped upward compared to support line 440, due to a large diameter section 436D (e.g. spanning over 2") of the lumbar region 436 and to allow sectional space for the sacral region 38. The support pattern is a continuous yet varying surface pattern along longitudinal axis 410 in between the first and second ends 420, 422. The elongated three-dimensional structure is substantially circular and substantially symmetrical around longitudinal axis 410 (i.e. transverse plane when referring to human anatomy) allowing the device the ability to roll around longitudinal axis 410 (i.e. side-to-side (see 412) for a person when laying on the device). Furthermore, when in use by a person the device substantially retains its elongated three-dimensional structure and therewith retains the rolling ability while in use. The circular pattern in the transverse plane might become a little more ellipsoidal, yet, and again, the device should be firm enough to retain its side-to-side rolling ability when in use.

More specifically, the vertebral surface pattern distinguishes different regions in a direction from first-end 420 to second-end 422 and defined by support-lines 440 and 442:
  Cranial-cervical region 430 with an axis projected and defined along longitudinal axis 410 and converging as first-end 420 with a first-end diameter defined in a plane perpendicular to longitudinal axis 410,
  Cervical region 432 with a major axis projected and defined along longitudinal axis and with a maximum cervical diameter 432D defined in a plane perpendicular to longitudinal axis 410,
  Thoracic region 434 with a major axis projected and defined along longitudinal axis and with a minimum thoracic diameter 434D defined in a plane perpendicular to longitudinal axis 410,
  Lumbar region 436 with a major axis projected and defined along longitudinal axis and with a maximum lumbar diameter 436D defined in a plane perpendicular to longitudinal axis 410, and
  Sacral region 438 with an axis projected and defined along longitudinal axis 410 and converging as second-end point 420 with a second-end diameter defined in a plane perpendicular to longitudinal axis 410.

Also, in this example, it is the arrangement of these regions in that particular order and with their respective surfaces that define the continuous and varying vertebral surface pattern.

There are a couple of specific features that are key to exemplary devices 100, 400 to be able to promote musculoskeletal alignment and strengthening of a vertebral system, and the ability to roll side-to-side with respect to a person as indicated by 212, 412 around respective longitudinal axes 210, 410, which are:

- The length defined along longitudinal axis 210 is shorter for cervical region 232 than lumbar region 236, likewise the length defined along longitudinal axis 410 is shorter for cervical region 432 than lumbar region 436.
- The length defined along longitudinal axis 210 is shorter for cranial-cervical region 230 than sacral region 238, likewise, the length defined along longitudinal axis 410 is shorter for cranial-cervical region 430 than sacral region 438, and
- Maximum cervical diameter 232D and the maximum lumbar diameter 236D are substantially identical and both larger than minimum thoracic diameter 234D, likewise maximum cervical diameter 432D and the maximum lumbar diameter 436D are substantially identical and both larger than minimum thoracic diameter 434D.

Figure 3:
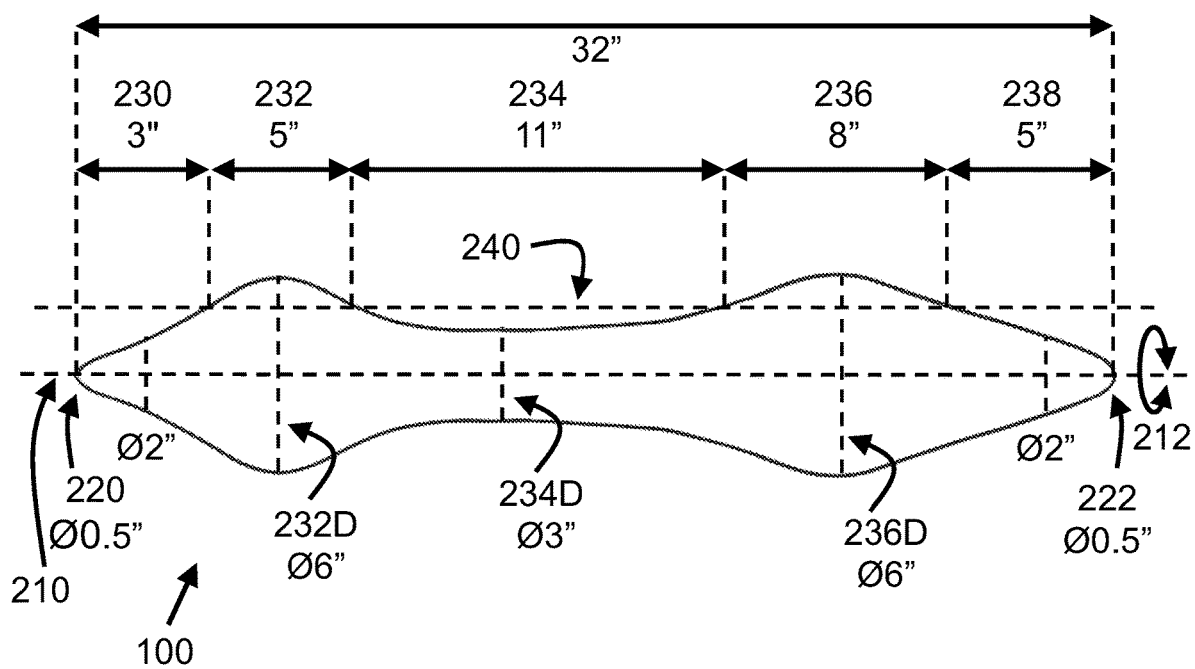

Exemplary dimensions for lengths and diameters pertaining and defining the regions are shown in FIGS. 3-4. Depending on the target size of people these dimensions could vary as a skilled artisan would appreciate. It is further noted, that in one example, the first-end diameter and the second-end diameter could substantially identical and smaller than the minimum thoracic diameter. In the specific examples, the first-end diameter and the second-end diameter could be about 0.5", with a 2" diameter at about 2" from their respective ends, and the minimum thoracic diameter about 3-4".

A reasonable ratio between the minimum thoracic diameter on the one hand and the maximum cervical or lumbar diameters on the other hand could be ranging from 0.4 to 0.5 or 0.35 to 0.6. For example, if the minimum thoracic diameter is 3" and the maximum cervical diameter is 6" the ratio is 0.5.

In a variation of the exemplary embodiments, while still referring to FIGS. 2-4, the different regions of the vertebral surface pattern could be defined as follows:

- A parabolic, hyperbolic or tapering cranial-cervical region 230, 430 with a major axis projected and defined along longitudinal axis 210, 410 and converging as the first-end with a first-end diameter defined in a plane perpendicular to longitudinal axis 210, 410,
- An ellipsoidal cervical region 232, 432 with a major axis projected and defined along longitudinal axis 210, 410 and with a maximum cervical diameter 232D, 432D defined in a plane perpendicular to longitudinal axis 210, 410,
- A hyperboloidal thoracic region 234, 434 with a major axis projected and defined along longitudinal axis 210, 410 and with a minimum thoracic diameter 234D, 434D defined in a plane perpendicular to longitudinal axis 210, 410,
- An ellipsoidal lumbar region 236, 436 with a major axis projected and defined along longitudinal axis 210, 410 and with a maximum lumbar diameter 236D, 436D defined in a plane perpendicular to longitudinal axis 210, 410, and
- A parabolic, hyperbolic or tapering sacral region 238, 438 with a major axis projected and defined along longitudinal axis 210, 410 and converging as the second-end point with a second-end diameter defined in a plane perpendicular to longitudinal axis 210, 410.

As a variation to these latter embodiments, the ellipsoidal cervical region could be an asymmetrical ellipsoidal cervical region defined along the longitudinal axis, the ellipsoidal lumbar region could be an asymmetrical ellipsoidal lumbar region defined along the longitudinal axis, and/or the hyperboloidal thoracic region could be an asymmetrical ellipsoidal lumbar region defined along the longitudinal axis. Asymmetric is defined by the minor axis of the shape when projected perpendicular on the major axis no longer defining two equal part along the major axis. For example, the minimum of the hyperboloidal thoracic region with respect to e.g. FIGS. 3 and 4 are shifted more to the left.

The device is preferably a single structure that can for example be made out of foam via an injection molding process. As skilled artisan would readily appreciate, various different materials or fabrication techniques could be used to obtain the objectives of the device, and the invention is not limited to foam or injection molding. Furthermore, a skilled artisan would appreciate that the device could be a solid structure, a hollow structure, a sectional structure, an inflatable structure or a combination thereof as long as the device when put to practice forms the single elongated three-dimensional structure as shown in e.g. FIG. 1. The device surface could be patterned or textured, yet still maintaining the vertebral support to a person's back as defined in view of FIGS. 2-4.

The device can be used as a personal training device or in a professional healthcare setting. Example of use are, but not limited to:

- Laying on the device in a parallel position, face up, arms out to the side or next to the body with palms facing up, knees bent and feet flat on the ground to help relax/realign the spine and/or to perform static posture exercise with no spinal movement and with/without arm/leg movement.
- Laying on the device in parallel manner, with knees straight and legs relaxed, arms out to the side, palms up, and rolling it side to side while performing deep breathing, or any dynamic stabilization exercise with or without arm/leg movement.
- The device can be used in sitting, standing, or supine position for deep breathing, posture correction, core strengthening in neutral position, activation of pelvic floor muscles and diaphragm.
- The device features two convex curves, smaller curve on one end is for head/neck alignment and larger convex curve is for lower back/tailbone alignment.
- The optimal alignment for proper use is determined once the person lays next to it, aligns self with proper ends and then rolls up on it. Person can then move up/down as needed to find the most optimal position.
- Another option for use is by directly laying on the device in a parallel manner and slides oneself up/down and/or gently/slowly to align spine with device to find the comfortable position.

What is claimed is:

1. A device to promote musculoskeletal alignment and strengthening of a vertebral system, comprising:
    an elongated three-dimensional single structure defining a longitudinal axis between a first-end and a second-end, a vertebral surface pattern for supporting the vertebral system extending as a continuous and varying surface pattern along the longitudinal axis in between the first and second ends, and wherein the elongated three-dimensional single structure is circular and symmetrical around the longitudinal axis defining the continuous and varying surface pattern,
    wherein the continuous and varying vertebral surface pattern distinguishes in a direction from the first-end to the second-end:

(i) a cranial-cervical region with an axis defined along the longitudinal axis and converging as the first-end with a first-end diameter defined in a plane perpendicular to the longitudinal axis,
(ii) a cervical region with a major axis defined along the longitudinal axis and with a maximum cervical diameter defined in a plane perpendicular to the longitudinal axis,
(iii) a thoracic region with a major axis defined along the longitudinal axis and with a minimum thoracic diameter defined in a plane perpendicular to the longitudinal axis,
(iv) a lumbar region with a major axis defined along the longitudinal axis and with a maximum lumbar diameter defined in a plane perpendicular to the longitudinal axis, and
(v) a sacral region with an axis defined along the longitudinal axis and converging as the second-end point with a second-end diameter defined in a plane perpendicular to the longitudinal axis,
wherein the regions are arranged in an order from (i) to (v) and their respective surfaces together define the continuous and varying vertebral surface pattern,
wherein the length defined along the longitudinal axis is shorter for the cervical region than for the lumbar region, and
wherein the length defined along the longitudinal axis is shorter for the cranial-cervical region than for the sacral region.

2. The device as set forth in claim 1, wherein the maximum cervical diameter and the maximum lumbar diameter are substantially identical and both larger than the minimum thoracic diameter.

3. The device as set forth in claim 1, wherein the minimum thoracic diameter relative to either or both the maximum cervical diameter and the maximum lumbar diameter is defined by a ratio of 0.3 to 0.6.

4. The device as set forth in claim 1, wherein the minimum thoracic diameter relative to either or both the maximum cervical diameter and the maximum lumbar diameter is defined by a ratio of 0.4 to 0.5.

5. The device as set forth in claim 1, wherein the device substantially retains the elongated three-dimensional structure when in use by a person.

6. The device as set forth in claim 1, wherein the device has the ability to roll around the longitudinal axis and retains the rolling ability when in use by a person.

7. The device as set forth in claim 1, wherein the device has the ability to roll around the cervical region and the lumbar region.

8. The device as set forth in claim 1, wherein the first-end diameter and the second-end diameter are substantially identical and smaller than the minimum thoracic diameter.

9. The device as set forth in claim 1, wherein the varying surface pattern is textured.

10. The device as set forth in claim 1, wherein the device is solid, hollow, or inflatable.

11. A device to promote musculoskeletal alignment and strengthening of a vertebral system, comprising:
an elongated three-dimensional single structure defining a longitudinal axis between a first-end and a second-end, a vertebral surface pattern for supporting the vertebral system extending as a continuous and varying surface pattern along the longitudinal axis in between the first and second ends, and wherein the elongated three-dimensional single structure is substantially circular and substantially symmetrical around and over substantially the entire or the entire longitudinal axis defining the continuous and varying surface pattern,
wherein the continuous and varying vertebral surface pattern distinguishes in a direction from the first-end to the second-end:
(i) a cranial-cervical region with an axis defined along the longitudinal axis and converging as the first-end with a first-end diameter defined in a plane perpendicular to the longitudinal axis,
(ii) a cervical region with a major axis defined along the longitudinal axis and with a maximum cervical diameter defined in a plane perpendicular to the longitudinal axis,
(iii) a thoracic region with a major axis defined along the longitudinal axis and with a minimum thoracic diameter defined in a plane perpendicular to the longitudinal axis,
(iv) a lumbar region with a major axis defined along the longitudinal axis and with a maximum lumbar diameter defined in a plane perpendicular to the longitudinal axis, and
(v) a sacral region with an axis defined along the longitudinal axis and converging as the second-end point with a second-end diameter defined in a plane perpendicular to the longitudinal axis,
wherein the regions are arranged in an order from (i) to (v) and their respective surfaces together define the continuous and varying vertebral surface pattern,
wherein the length defined along the longitudinal axis is shorter for the cervical region than for the lumbar region, and
wherein the length defined along the longitudinal axis is shorter for the cranial-cervical region than for the sacral region.

12. The device as set forth in claim 11, wherein the maximum cervical diameter and the maximum lumbar diameter are substantially identical and both larger than the minimum thoracic diameter.

13. The device as set forth in claim 11, wherein the minimum thoracic diameter relative to either or both the maximum cervical diameter and the maximum lumbar diameter is defined by a ratio of 0.3 to 0.6.

14. The device as set forth in claim 11, wherein the minimum thoracic diameter relative to either or both the maximum cervical diameter and the maximum lumbar diameter is defined by a ratio of 0.4 to 0.5.

15. The device as set forth in claim 11, wherein the device substantially retains the elongated three-dimensional structure when in use by a person.

16. The device as set forth in claim 11, wherein the device has the ability to roll around the longitudinal axis and retains the rolling ability when in use by a person.

17. The device as set forth in claim 11, wherein the device has the ability to roll around the cervical region and the lumbar region.

18. The device as set forth in claim 11, wherein the first-end diameter and the second-end diameter are substantially identical and smaller than the minimum thoracic diameter.

19. The device as set forth in claim 11, wherein the varying surface pattern is textured.

20. The device as set forth in claim 11, wherein the device is solid, hollow, or inflatable.

* * * * *